United States Patent [19]
Fukunishi

[11] Patent Number: 5,297,226
[45] Date of Patent: Mar. 22, 1994

[54] LIGHT GUIDE CONNECTOR

[75] Inventor: Souhei Fukunishi, Tochigi, Japan

[73] Assignee: Kabushiki Kaisha Toshiba, Kawasaki, Japan

[21] Appl. No.: 761,229

[22] Filed: Sep. 17, 1991

[30] Foreign Application Priority Data

Sep. 18, 1990 [JP] Japan .................... 2-246233

[51] Int. Cl.⁵ .............................................. G02B 6/40
[52] U.S. Cl. ...................................... 385/54; 385/115
[58] Field of Search .................. 385/54, 115, 116, 117, 385/118, 119, 120, 121

[56] References Cited

U.S. PATENT DOCUMENTS

| | | | |
|---|---|---|---|
| 3,669,772 | 6/1972 | Strack | 156/15 |
| 3,914,015 | 10/1975 | McCartney | 385/54 |
| 4,080,045 | 3/1978 | Nakatsubo et al. | 385/115 |
| 4,252,408 | 2/1981 | Parsons et al. | 385/115 |
| 4,360,372 | 11/1982 | Maciejko | 385/115 |
| 4,547,040 | 10/1985 | Yamamoto et al. | 385/115 |
| 5,013,128 | 5/1991 | Stern et al. | 385/115 |
| 5,061,035 | 10/1991 | Rogers | 385/115 |

FOREIGN PATENT DOCUMENTS

| | | |
|---|---|---|
| 0068175 | 1/1983 | European Pat. Off. |
| 3725693 | 2/1988 | Fed. Rep. of Germany |
| 2191873 | 12/1987 | United Kingdom |
| 91/02993 | 3/1991 | World Int. Prop. O. |

*Primary Examiner*—Rodney B. Bovernick
*Assistant Examiner*—Robert E. Wise
*Attorney, Agent, or Firm*—Foley & Lardner

[57] ABSTRACT

A light guide connector is formed at each end of a light guide to connect the light guide to another one. The light guide reduces leakage of light energy even if optical axes of optical fibers of opposing light guide to be connected are not aligned with one another. Optical fibers in the connector are bonded with one another with an adhesive having a smaller refractive index than that of cladding of the optical fibers. Claddings of the optical fibers are melted and solidified with same solvent as the cladding.

7 Claims, 7 Drawing Sheets

LIGHT GUIDE CONNECTOR

BACKGROUND OF THE INVENTION

1. Field of the Invention

The present invention relates to a structure of a connector of a light guide having a bundle of optical fibers for transmitting light energy from a light source.

2. Description the Prior Art

Light guides are widely used as means transmitting light energy from a light source to a target part, for example, in an endoscope.

Figure 1:
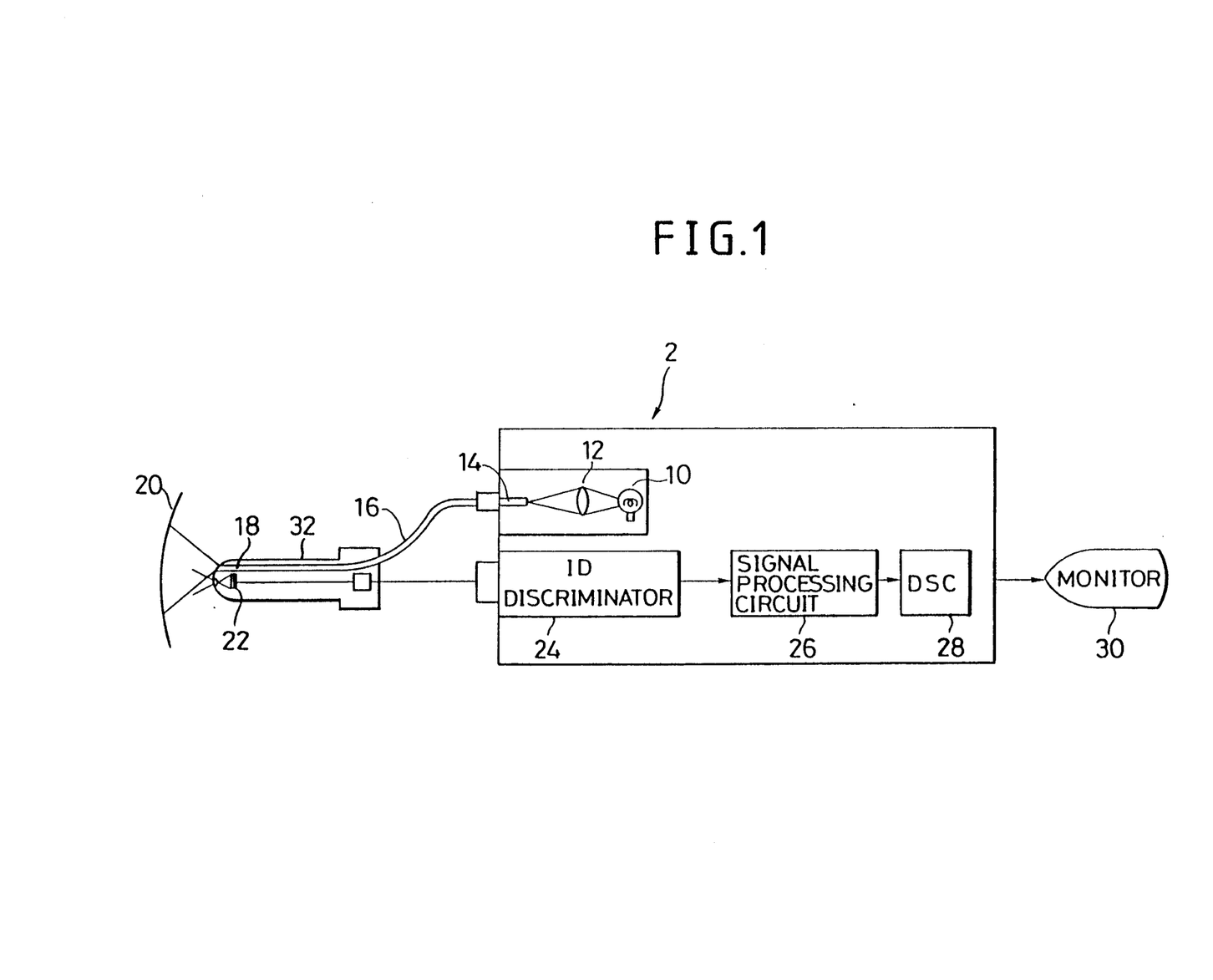
FIG. 1 is a schematic view showing an endoscope.

FIG. 1 is a schematic view showing the endoscope for photographing a part of human body cavity and displaying an image of the photographed part on a monitor. In the figure, an endoscope apparatus 2 has a light source 10 for emitting light, which is collected by a condenser lens 12 and send to light receiving unit 14. The light is then transmitted to an illumination unit 18 through a light transmission unit 16, for illuminating a target part in a human body cavity. A sensor 22 photographs the target part and provides image informations to be processed by circuits such as 24, 26, 28 shown in FIG. 1. Processed signals are sent to a monitor from the circuits and then, the photographed image is displayed on a monitor 30.

The light transmitting unit 16 is usually a light guide comprising a bundle of optical fibers. Each optical fiber comprises a core transmitting light energy and a glass cladding around the core for preventing light leakage. The light guide 16 is usually accommodated in an inserting means which is inserted into along a human body cavity, so that the inserting means and light guide must be flexible. This requirement induces that the light guide should comprise a bundle of thin optical fiber elements.

Figure 2:
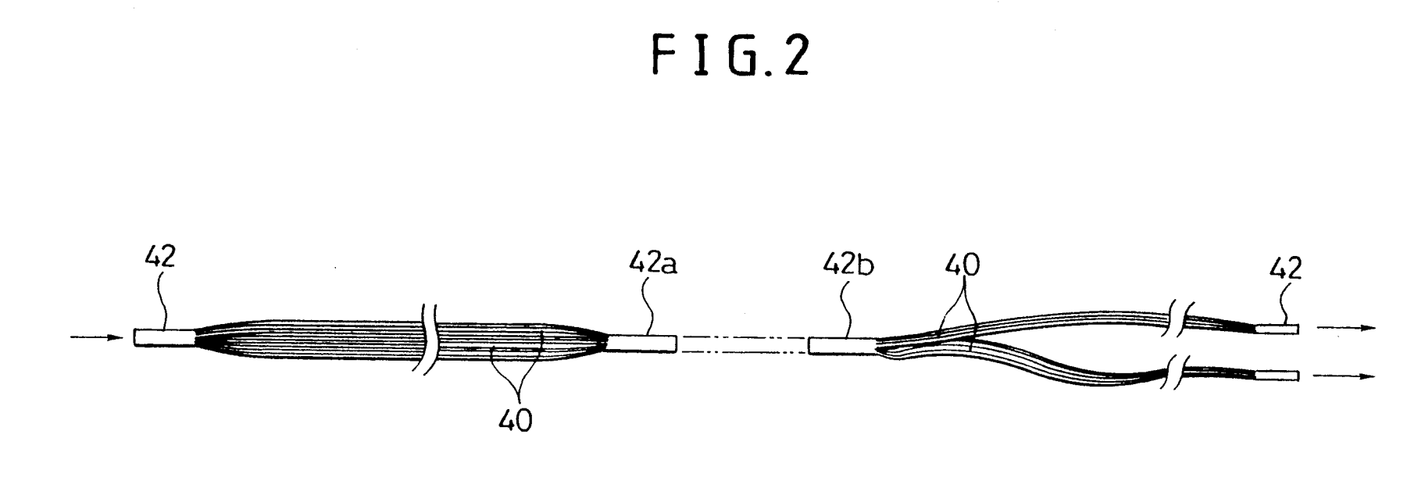
FIG. 2 is a view showing connectors of a light guide.

From the view points of manufacturing, maintenance and handling, the light guide is preferred to be properly divided into sections and connected to one another with connectors. It is practically difficult, however, to provide a connector to each of a lot of the thin optical fiber elements. Then, optical fiber elements 40 are, as shown in FIG. 2, bonded together to form connectors 42, 42a or 42b. End faces of the connectors 42a and 42b are tightly attached to one another in order to transmit enough light energy.

However, since it is difficult to align each center axis of the optical fiber elements of opposing connectors 42a and 42b when attaching them to each other, a great deal of the light energy is lost. This light energy loss causes problems that it generates heat loss and requires a light source of a large power.

SUMMARY OF THE INVENTION

An object of this invention is to provide a light guide connector which does not cause a great deal of light energy loss. In order to accomplish this object, the present invention provides light guide connectors which have large light emitting area in an emitting end and large light receiving area in a receiving end, particularly, at least the large light receiving area in the receiving end. This way prevents the connectors from losing the light energy in attached faces of the connectors.

The connectors by the present invention are made by bonding the thin optical fiber elements in the connector with a light transmitting adhesive having a smaller refractive index than that of the cladding. Then, a projected light from the emitting end enters into the adhesive part of the receiving end and advances in the adhesive part to enter into the cores of the connectors 42b. The light is advancing in the core towards the illumination unit 18.

Therefore, with the connectors by the present invention, the total transmission of light energy from the light emitting connector 42a to the light receiving connector 42b is increased, that is, a leakage of light energy due to a disagreement in optical axes of the thin optical fiber elements opposing connectors is reduced.

The increment in the total transmission of light energy can be also achieved by using the following connectors: a connector made by melting the cladding part of the light guide to increase the number of the optical fiber cores accommodated in the connector, or a connector made by fusing the cladding part with a solvent of the same kind as the cladding to fill gaps between the optical fibers to increase the volume of the cladding in the connector.

As mentioned above, since the light receiving area of connector 42b is substantially expanded, the leakage of light energy at the attached ends of the connectors is reduced, and the problem that each optical axis of the fiber elements disagrees with each other is solved.

In this way, the present invention reduces the optical loss and heat generated by the loss and thus reduces the size of the connector. The connector according to the invention is easily fabricated at a low cost, since the optical axes of optical fibers of opposing connectors are not required to precisely align with each other.

These and other objects, features and advantages of the present invention will be more apparent from the following detailed description of the preferred embodiment in conjunction with the accompanying drawings.

DETAILED DESCRIPTION OF THE EMBODIMENTS

Figure 3:
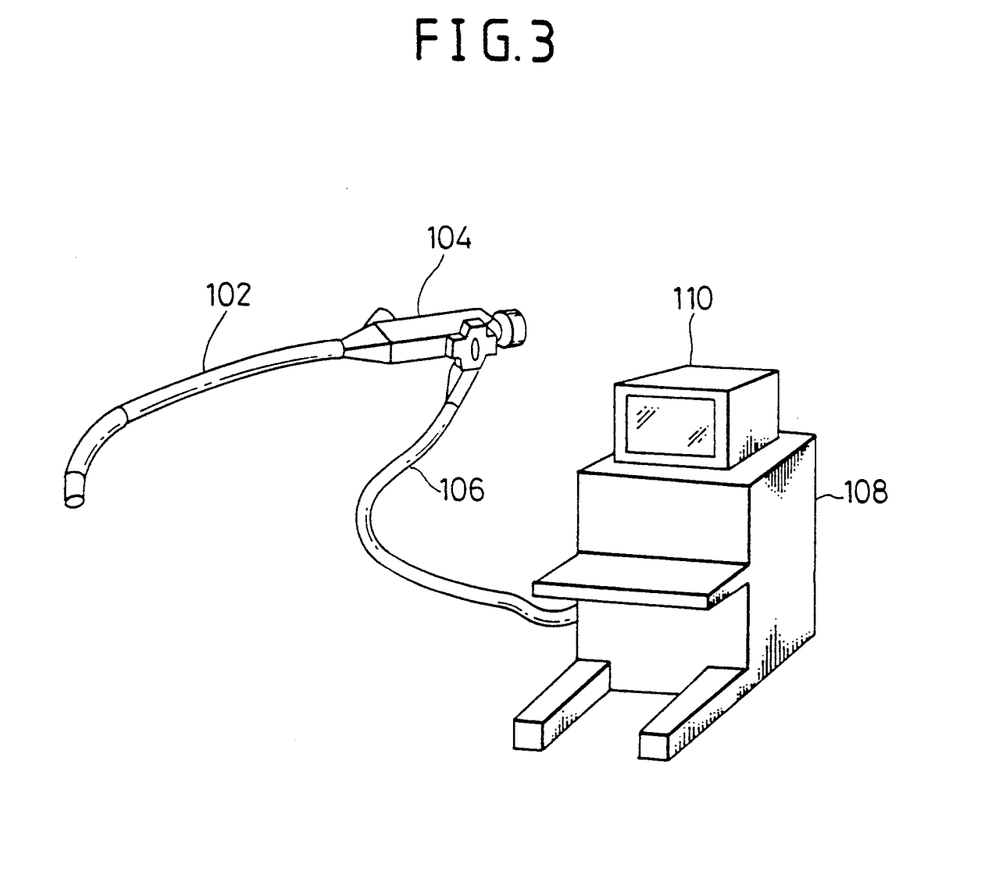
FIG. 3 is a perspective view showing the endoscope.

FIG. 3 is a perspective view showing an endoscope employing the present invention.

The endoscope comprises an intermediate tube 102 to be inserted into a human body cavity, a control unit 104 arranged at the base of the intermediate tube 102, a universal cord 106 connected to the control unit 104.

The universal cord 106 is connected to an electronic endoscope apparatus 108. The apparatus 108 incorporates a light source 10 for generating light to illuminate an inspection target part in the body cavity 20 as shown in FIG. 1. The apparatus 108 incorporates information processing unit 26 for processing signals from a photographing elements 22 such as a CCD disposed inside a head end portion of the intermediate tube 102.

The photographing element 22 receives reflected light from the inspection target part 20 in the body cavity, and converts an optical image formed by the reflected light into electric signals, which is sent to the information processing unit 26 in the endoscope apparatus 108. An output signal from the information processing unit 26 is sent to a monitor 110 such as CRT display unit, on which an image of the surface of the inspection target part in the human body cavity is displayed.

The intermediate tube 102, control unit 104 and universal cord 106 are incorporated by a light guide having connectors which connect these units. The light guide transmits light energy from the light source 10 to a illumination window 18 formed at the head end portion of the intermediate tube 102, and the light illuminates the inspection target part.

As shown in FIG. 2, the light guide comprises a bundle of optical fibers elements 40. The bundle of optical fibers is not continuous from the light source to the illumination window, but divided into sections and connected to one another with connectors formed at ends of each guide section. If the light leaks or attenuates at the connectors, the light is not fully transmitted, thereby requiring a light source of a large power. Furthermore heat may be generated to hinder the compactness of each connector.

To avoid these problems, the present invention proposes several embodiments of the light guide connectors.

Figure 4A:
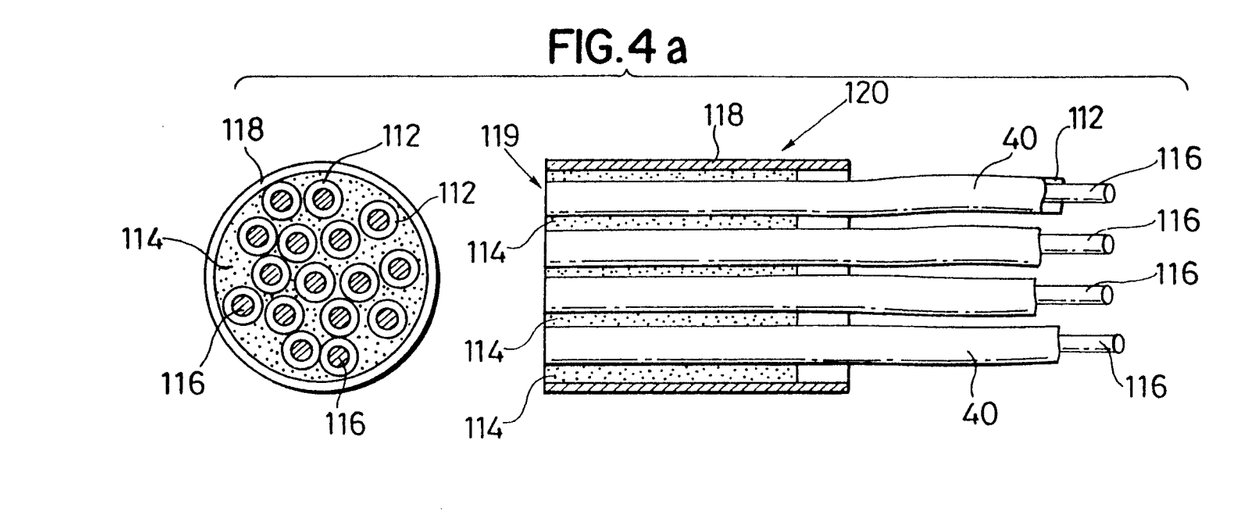
FIGS. 4(a) to 4(c) are views showing connectors of a light guide according to embodiment of the invention.

FIG. 4(a) shows a light guide connector according to the present invention. Each end of optical fiber element 40 made of multicomponent glass fiber is bonded to one another with a transmitting adhesive 114 having a smaller refractive index than that of cladding 112 disposed around each of the optical fiber element 40, to form a connector 120.

Namely, to fabricate the connector 120, an end of each optical fiber element 40 is inserted into a connector cylinder 118 and held such that each of the optical fiber elements 40 are substantially in parallel with a center axis of the connector cylinder 118. Thereafter, the adhesive 114 is applied and solidified. The adhesive is an optical adhesive such as an epoxy-based adhesive or an acrylic adhesive having a low refractive index.

To improve the transmission of light energy and to prevent the scattering of light, an end face 119 of the connector 120 on each of the light emitting and receiving end faces of the light guide must be properly polished.

Figure 5:
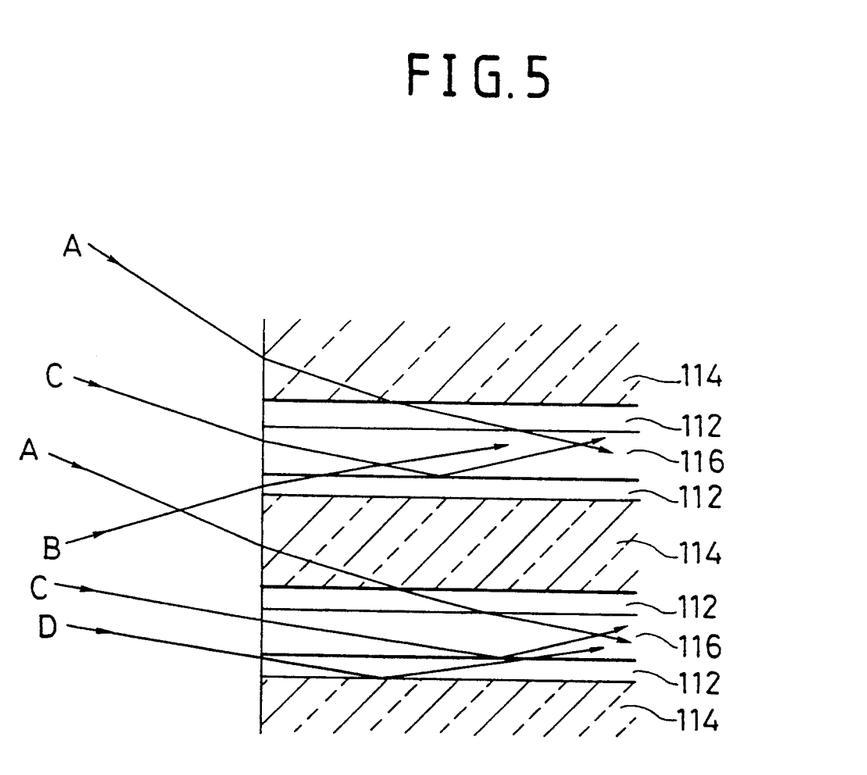
FIG. 5 is a view explaining a principle of the invention.

FIG. 5 shows the effect of the invention where the quantity of transmitted light energy is improved.

Generally, the angle of refraction of light becomes smaller when the light enters into a substance having a large refractive index from a substance having a small refractive index. On the other hand, when light advances towards a substance having a small refractive index from a substance having a large refractive index at an incident angle greater than the critical angle, the light is totally reflected on a surface of the substance having the small refractive index.

In FIG. 5, the refractive index n3 of the adhesive 114 is smaller than the refractive index n2 of the cladding 112, so that a light beam A entering adhesive 114 is refracted by the surface of the cladding 112 such that the light beam A will be more in parallel with an axis of the optical fiber element 40. A refractive index n1 of the core 116 is usually larger than the refractive index n2 of the cladding 112, so that a light beam B entering the cladding 112 will be more parallel with an axis of the optical fiber element 40 when entering the core 116.

Namely, light beams entering adhesive 114 tend to enter the core 116 through the cladding 112, and light beams entering the cladding 112 also tend to enter the core 116. In this way, both the light beams entering the adhesive 114 and cladding 112 tend to enter the core 116. On the other hand, the light beams D advancing in the cladding 112 are totally reflected by the adhesive 114, while light beams C advancing in the core 116 are totally reflected by the cladding 112.

As a result, light beam entering the adhesive 114 at an incident angle within a certain range enter the core 116 through the cladding 112, thereby increasing the quantity of light beams passing through the core 116. This is true, however, only when there is no optical attenuation and the connector has infinite length. It is physically impossible and not required because of optical attenuation to infinitely extend the length of the connector.

Figure 6:
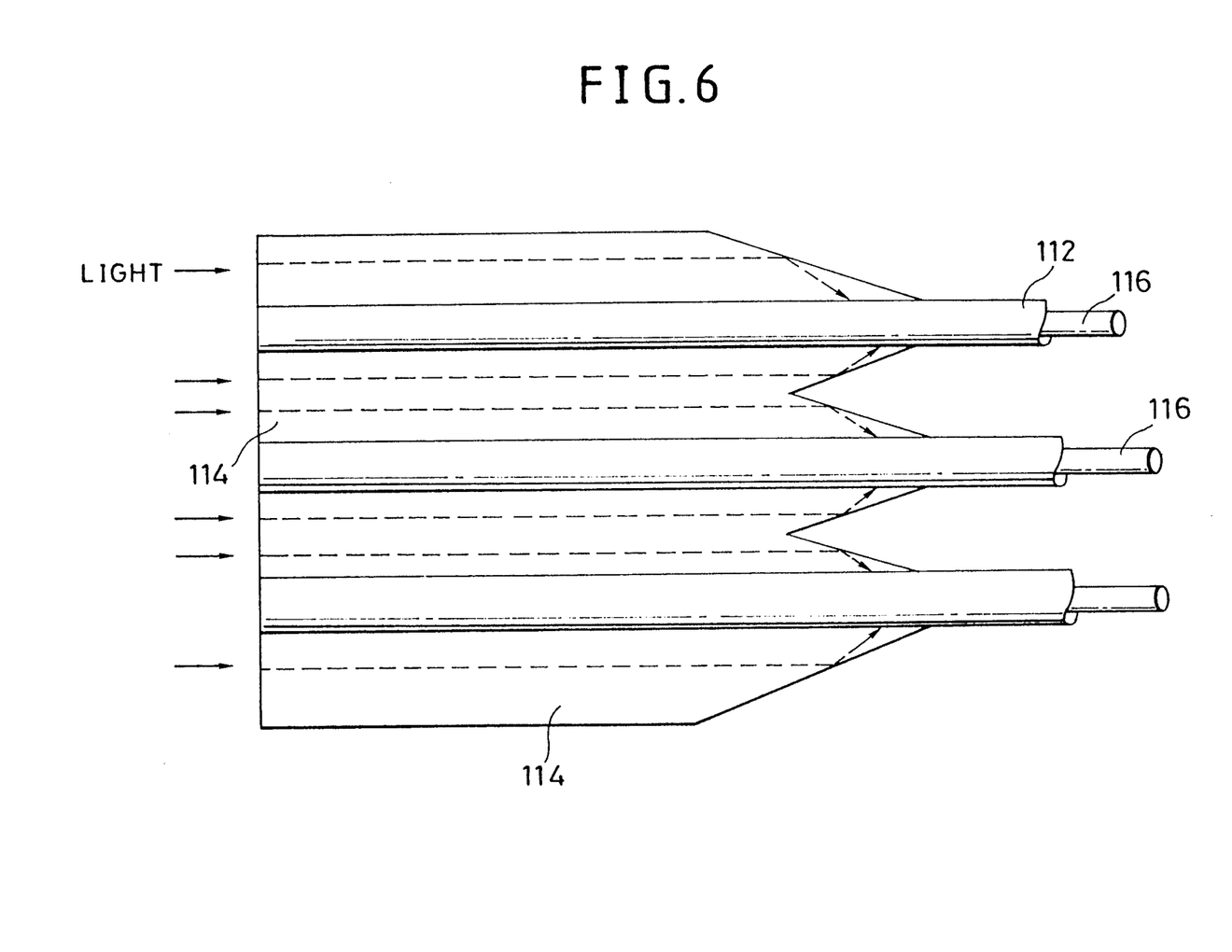
FIG. 6 is a view showing a connector having slopes.

According to the embodiment, the length of the connector 120 is about 20 to 30 mm. If the connector 120 is too short, the surface of the adhesive 114 in the vicinity of an end of the connector 120 may be sloped as shown in FIG. 6. In this case, a light beam indicated with dotted line advancing in parallel in the adhesive 114 is totally reflected by the slope to enter the cladding 112 or the core 116. In FIG. 6, the adhesive 114 as a whole is not sloped but divided into small zones and sloped.

Figure 4B:
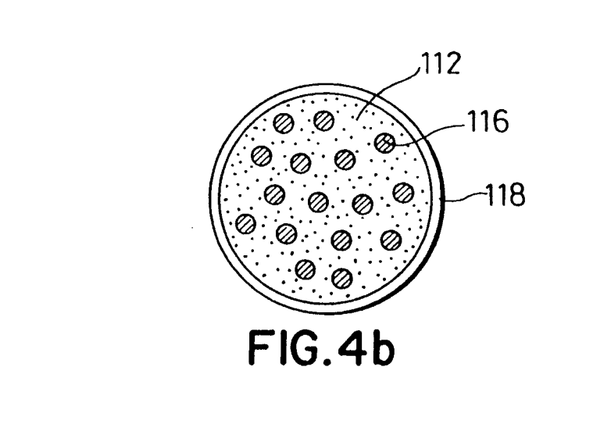

FIG. 4(b) shows a connector of the light guide according to another embodiment of the invention. This embodiment employs the same material as the cladding 112 and melts and solidifies the cladding 112 in the connector. Namely, the cross-sectional area of the cladding in the connector is increased to substantially increase the light receiving area of the light guide.

Due to the same reasons as mentioned before, light beams entering the cladding 112 enter the cores 116, thereby increasing the quantity of light beams transmitted through the cores 116. The cladding 112 is melted and solidified through melt coupling or diffusion coupling with use of, for example, a $B_2O_3SiO_2$-based glass adjuvant.

Figure 4C:
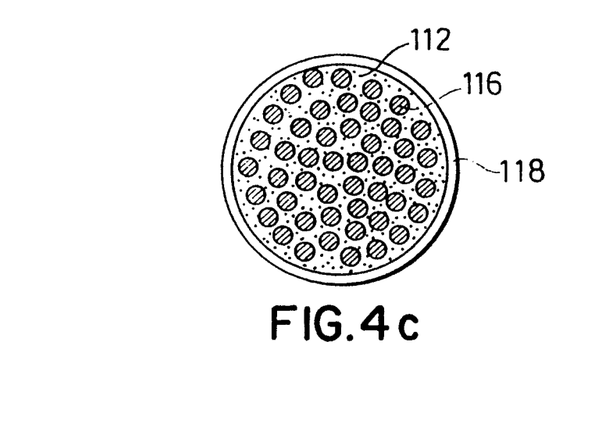

FIG. 4(c) shows a connector of the light guide according to still another embodiment of the invention. This embodiment melts and solidifies the cladding 112 itself to increase the number of the cores 116 in the connector, i.e., the total cross-sectional area of the cores 116. This arrangement also increases the quantity of transmitted light.

If the number of the optical fiber elements 40 in a light receiving end is too many, the optical fibers 40 may be optically coupled to reduce the number of the light guide.

In this way, the light receiving area at the connecting end of the light guide for an endoscope is substantially increased, and therefore, a disagreement in the optical fibers of opposing connectors will not cause serious trouble. Since the connector is solidified in an airtight manner, it secures a waterproofing effect.

Figure 7A:
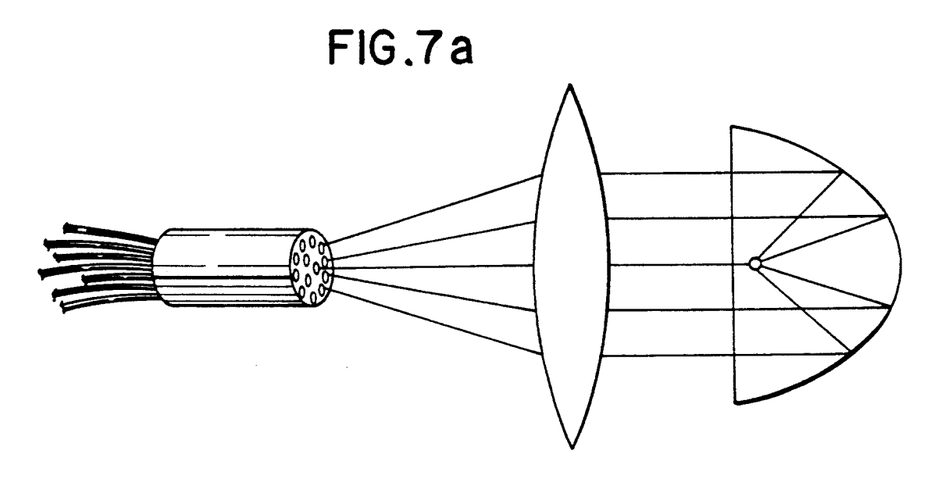
FIGS. 7(a) and 7(b) are views showing a light receiving element according to the invention.
Figure 7B:
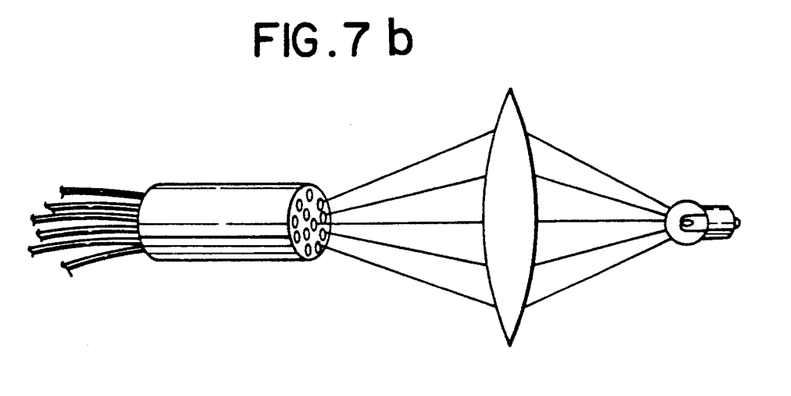

FIGS. 7(a) and (b) show connectors of a light guide according to the invention, serving as a light receiving element or a light receiving unit of a light source. These examples also show an increase in the quantity of transmitted light with use of the means mentioned above.

Various modifications will become possible for those skilled in the art after receiving the teachings of the present disclosure without departing from the scope thereof.

What is claimed is:

1. A light guide, comprising:

a bundle of separate optical fiber elements for transmitting light; and a connector for removably connecting sections of said light guide to one another, wherein said connector is obtained by melting and solidifying together a cladding around a core of each of said separate optical fiber elements at an end portion of said separate optical fiber elements, wherein a cross-section area of said cladding in said connector and a light receiving area of said light guide is increased, said solidified end portion having a length such that optical attenuation in said cladding is completely achieved.

2. A light guide as claimed in claim 1, wherein said cladding is melted and solidified through a melt coupling process or a diffusion coupling process.

3. A light guide, comprising:
a bundle of separate optical fiber elements for transmitting light; and a connector for removably connecting sections of said light guide to one another, said connector being formed by bonding said separate optical fiber elements to one another at an end portion thereof with a transmitting adhesive, said transmitting adhesive having a refractive index, $n_3$, which is smaller than a refractive index, $n_2$, of a cladding disposed around a core of each of said separate optical fiber elements, wherein said refractive index, $n_2$, of said cladding is smaller than a refractive index, $n_1$, of said core, wherein an end surface of said transmitting adhesive is divided into a plurality of sectionally sloped surfaces, said sectionally sloped surfaces totally reflecting light passing through said transmitting adhesive into a core of an optical fiber element.

4. A light guide as claimed in claim 3, wherein said transmitting adhesive is an optical adhesive such as an epoxy-based adhesive or an acrylic adhesive.

5. A light guide, comprising:
a bundle of separate optical fiber elements for transmitting light; and a connector for removably connecting sections of said light guide to one another, said connector being formed by bonding said separate optical fiber elements to one another at an end portion thereof with a transmitting adhesive, said transmitting adhesive having a refractive index, $n_3$, which is smaller than a refractive index, $n_2$, of a cladding disposed around a core of each of said separate optical fiber elements, wherein said refractive index, $n_2$, of said cladding is smaller than a refractive index, $n_1$, of said core, wherein a length of said end portion bonded with said transmitting adhesive is such that complete optical attenuation in said transmitting adhesive is substantially achieved.

6. A light guide as claimed in claim 5, wherein said length of said connector is about 20 to 30 mm.

7. A light guide, comprising:
a bundle of separate optical fiber elements for transmitting light; and a connector for removably connecting sections of said light guide to one another, wherein said connector is obtained by melting and solidifying together a cladding around a core of each of said separate optical fiber elements at an end portion of said separate optical fiber elements such that a cross-section area of said cladding in said connector and a light receiving area of said light guide is increased, wherein said separate optical fiber elements are placed in a closely packed circular configuration, thereby increasing the number of the fiber optical elements in the connector.

* * * * *